(12) United States Patent
Morris

(10) Patent No.: US 9,589,225 B2
(45) Date of Patent: Mar. 7, 2017

(54) RFID TAG FOR CRYOGENIC STRAWS

(71) Applicant: CRYOGATT SYSTEMS LIMITED, Buxted (GB)

(72) Inventor: Geoffrey Morris, Pinner (GB)

(73) Assignee: Cryogatt Systems Limited, Buxted Sussex (GB)

( * ) Notice: Subject to any disclaimer, the term of this patent is extended or adjusted under 35 U.S.C. 154(b) by 0 days.

(21) Appl. No.: 14/410,945

(22) PCT Filed: Jun. 28, 2013

(86) PCT No.: PCT/GB2013/051731
§ 371 (c)(1),
(2) Date: Dec. 23, 2014

(87) PCT Pub. No.: WO2014/001819
PCT Pub. Date: Jan. 3, 2014

(65) Prior Publication Data
US 2015/0379390 A1    Dec. 31, 2015

(30) Foreign Application Priority Data
Jun. 29, 2012   (GB) .................................. 1211766.9

(51) Int. Cl.
| | | |
|---|---|---|
| *G06F 17/00* | (2006.01) |
| *G06K 19/077* | (2006.01) |
| *A01N 1/02* | (2006.01) |
| *B01L 3/00* | (2006.01) |
| *G06K 19/04* | (2006.01) |

(52) U.S. Cl.
CPC ..... *G06K 19/07758* (2013.01); *A01N 1/0268* (2013.01); *B01L 3/5453* (2013.01); *G06K 19/041* (2013.01); *G06K 19/07779* (2013.01); *B01L 2300/022* (2013.01); *B01L 2300/0838* (2013.01); *B01L 2300/0887* (2013.01); *B01L 2300/1894* (2013.01)

(58) Field of Classification Search
USPC .................................. 235/375, 492; 340/10.1
See application file for complete search history.

(56) References Cited

U.S. PATENT DOCUMENTS

| | | | |
|---|---|---|---|
| 7,350,703 B2 | 4/2008 | Ambartsoumian | |
| 2005/0247782 A1 | 11/2005 | Ambartsoumian | |
| 2008/0035642 A1* | 2/2008 | Esser .................. | B01L 3/5082 220/315 |
| 2008/0220507 A1 | 9/2008 | Clairaz | |

(Continued)

FOREIGN PATENT DOCUMENTS

| | | |
|---|---|---|
| CN | 201197939 | 2/2009 |
| EP | 2 315 163 A1 | 4/2011 |

(Continued)

OTHER PUBLICATIONS

The International Search Report corresponding to the PCT/GB2013/051731 application filed Jun. 28, 2013.

(Continued)

*Primary Examiner* — Ahshik Kim
(74) *Attorney, Agent, or Firm* — Kilpatrick Townsend & Stockton LLP

(57) ABSTRACT

A sleeve for a cryogenic straw, the sleeve comprising an RFID tag.

15 Claims, 3 Drawing Sheets

(56) References Cited

U.S. PATENT DOCUMENTS

| | | | |
|---|---|---|---|
| 2010/0107560 A1* | 5/2010 | Ehrsam | B01L 3/50825 53/375.9 |
| 2010/0302040 A1 | 12/2010 | Davidowitz | |
| 2011/0025467 A1* | 2/2011 | Longhurst | G02B 6/447 340/10.1 |
| 2011/0199187 A1 | 8/2011 | Davidowitz | |
| 2011/0239791 A1 | 10/2011 | Fici | |
| 2011/0318818 A1* | 12/2011 | Beau | A61D 19/024 435/284.1 |

FOREIGN PATENT DOCUMENTS

| | | |
|---|---|---|
| GB | 2 450 531 A | 12/2008 |
| GB | 2013/051731 | 6/2013 |
| JP | 2007066011 | 3/2007 |
| KR | 2010-0066958 | 6/2010 |
| WO | 2005/109332 A1 | 11/2005 |
| WO | 2005/115621 | 12/2005 |
| WO | 2005/115621 A1 | 12/2005 |
| WO | 2009/004366 A1 | 1/2009 |

OTHER PUBLICATIONS

IVF Witness document, Research Instruments Ltd. (Applicant became aware of this document in 2004).

* cited by examiner

RFID TAG FOR CRYOGENIC STRAWS

CROSS-REFERENCE TO RELATED APPLICATIONS

This application is a U.S. National Stage of PCT Application No. PCT/GB2013/051731, filed Jun. 28, 2013, which claims priority to Foreign Application No. 1211766.9 GB, filed Jun. 29, 2012, the entire contents of each of which are incorporated herein by reference in their entirety for all purposes.

TECHNICAL FIELD

The present invention relates to an RFID tag for cryogenic straws.

BACKGROUND

Biological samples may be preserved by cryogenic freezing. The biological samples are usually stored in disposable containers (disposables). The shape of the disposable container used depends on the type of sample. Examples of commonly used disposable containers include vials, straws and bags. The disposable container is stored at low temperatures in a Dewar flask typically filled with liquid nitrogen at a temperature of −196° C.

Where samples are stored in straws, a plurality of straws are usually kept in a visotube, a plurality of visotubes are in turn typically kept in a goblet, and a plurality of goblets are kept in a canister which is stored in the Dewar.

Stored biological samples can be identified by writing on the disposable containers themselves, or by labels stuck to the containers. These labels may be handwritten or printed and can include bar codes. However, such methods of identification have associated disadvantages; written notes on containers can easily be erased or smudged and labels containing handwritten notes and printed text or barcode information can fall off the disposable containers while they are stored inside the Dewar leading to unidentifiable samples. These problems are exacerbated by the cold conditions in which biological samples must be kept.

When performing an audit of biological samples stored in cold storage (at temperatures of −196° C.), the samples should not be allowed to warm up to a temperature greater than −130° C. It is therefore desirable to minimise the amount of time spent outside of the Dewar wherever possible.

Recording, monitoring and auditing of samples in cold storage takes a considerable amount of time and effort, even when samples are labelled using barcodes. An additional and undesirable increase in the time taken to record or audit samples arises as a result of frost which forms on the surfaces of disposable containers and their labels when they are removed from liquid nitrogen into relatively warmer temperatures. It is common for samples to be stored for many years (e.g. 15 years) but even after just one year in storage, the layer of frost which builds up on a disposable container can make it impossible to make an optical reading of a bar code on a label using a bar code reader because a layer of frost blocks or diffracts the light of the bar code reader. The container cannot be warmed up to remove frost as this would lead to destruction of the sample. The frost can be wiped off the disposable container but this contributes to an undesirable increase in the amount of time taken to read the sample.

It is known that Radio Frequency ID (RFID) tags can be used to monitor a plurality of disposable containers stored at low temperatures of down to −196° C. An RFID reader can be used to write information to and read information from the RFID tag before, after, or during cryogenic storage.

An RFID tag includes an RF transmitter and an RF receiver. An RFID reader can be used to transmit an encoded radio signal to a tag to interrogate it. Upon receiving the interrogation signal, the RFID tag transmits its identification information to the reader. This identification information may be a unique serial number assigned to a particular patient or a particular sample.

In Europe and other countries outside of the US, RFID components for medical storage operate at an approved frequency of 13.56 MHz. It is important that the frequency used for the RFID tag does not lead to any undesirable interference with other electronic medical equipment. Lower medically approved frequency bands such as 125 KHz do not provide enough signal bandwidth to provide the tag with a useful user defined memory.

EP2315163 discloses RFID tags that can be inserted into straws. Biological material is drawn into a straw via a "sucking" process. The location of an RFID tag in a straw takes up space inside of the straw. In addition, the placement of an RFID tag inside the straw impedes the ability to draw air and the material from container to straw, regardless of which end of the straw the RFID tag is inserted with respect to the sucking action. The location of the RFID tag inside the straw also means that the size of RFID tag used must be limited to a size smaller than the inner diameter of the straw.

WO 2005/115621 describes tagging of cryogenic straws using write-on or printable adhesive labels having an RFID tag attached thereto or incorporated therein. This method has the disadvantage that it relies upon the adhesive label retaining its adhesive properties. The longer the straw is kept under cryogenic conditions and the more times the goblet of tubes is accessed, the more likely it is that the adhesive will fail. In addition, the label is usually stuck to the straw by hand. A significant amount time and considerable amount of care is required to ensure that the adhesive label is correctly applied and therefore less likely to fall off during storage.

STATEMENT OF INVENTION

Accordingly, the present invention aims to solve the above problems by providing, according to a first aspect, a sleeve according to claim 1.

In this way, the ease and reliably with which a straw can be tagged with an RFID tag is improved as the RFID tag can be located on the straw by simply sliding the sleeve onto the straw to form a push-fit so that the sleeve is held in place around the straw by friction.

Furthermore, the size of the RFID tag is not limited by the inner diameter of the straw and the location of the RFID tag does not interfere with the positioning of the biological sample inside the straw.

Preferably, the sleeve has a tubular body.

The skilled person would understand the term tubular body to mean an elongate hollow body which has a cross section which is circular, oval, or any other continuous shape capable of completely encircling the outer circumference of a cryogenic straw.

Preferably, the tubular body is open at both ends.

Preferably, the tubular body has a circular cross section along a plane perpendicular to its longitudinal axis.

Preferably, the tubular body is rigid.

Preferably, the thickness of the tubular body is no more than 0.5 mm.

Preferably the tubular body has an inner diameter which is no less than 3.85 mm and no more than 4.05 mm.

The sleeve preferably has a length along its longitudinal axis which is no less than 2 mm and no more than 135 mm.

The RFID tag is preferably attached to the sleeve by an outer tubing.

The outer tubing is preferably heat shrink tubing. In this way, attachment of the RFID tag to the sleeve is achieved even after prolonged storage at cryogenic temperatures as the heat shrink tubing can withstand cryogenic temperatures such as −196° C.

According to a second aspect of the present invention, there is provided a cryogenic straw according to claim 10.

Preferably, the sleeve is crimped to the straw. The crimp provides a secure attachment that can withstand cryogenic temperatures.

In this way, the straw and sleeve are secured to one another at the "crimp". The location of the crimp relative to the length of the straw may be chosen to be the same for each of a plurality of straws. The crimp can therefore act as a locating means to ensure that the sleeve of each one of a plurality of straws is located at the same point on each straw.

The position of the sleeves relative to the straws can be chosen so that when one or more straws are stored in a given location, the positions of the RFID tag(s) are aligned with the position of an RFID reader. By positioning all sleeves (and therefore all RFID tags) at a given position relative to the straw, the ease and speed at which multiple RFID tagged straws can be read is improved.

According to a third aspect of the present invention, there is provided a method of labelling a cryogenic straw according to claim 12. The process of sliding the sleeve onto the straw is quick and easily reproducible so that the time taken for the electronic tag to be applied to the straw is minimised and the risk of human error reduced.

The method of labelling the cryogenic straw preferably further comprises the step of crimping the sleeve onto the straw.

The present invention will now be disclosed by way of example only, with reference to the accompanying figures, in which.

DESCRIPTION

Figure 1:
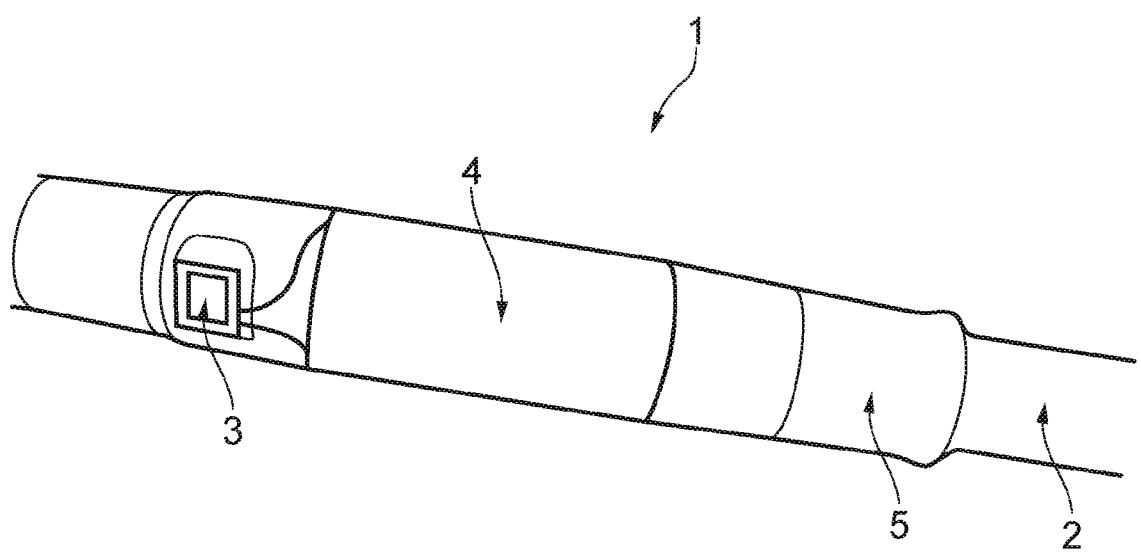
FIG. 1 is a picture of a sleeve.

FIG. 1 shows a sleeve 1 for a cryogenic straw. The sleeve has a tubular body 2 and includes an RFID tag. The RFID tag is made up of an RFID chip 3 and a tag antenna 4. The tag antenna 4 is formed from a copper wire looped around the tubular body 2 to form a coil. The ends of the copper wire are connected to the RFID chip 3. A protective coating 5 which can be an outer tubing such as heat shrink tubing is used to cover the RFID chip 3 and tag antenna 4 of the RFID tag and thereby attach the RFID tag to the tubular body 2.

As can be seen in FIG. 1, the tubular body 2 is a tube which is open at both ends. The sleeve is therefore capable of being fitted around a cryogenic straw without obstructing the ends of the cryogenic straw. This is advantageous because it is possible to position the sleeve onto the straw before a sample is sucked into the straw.

Figure 2:
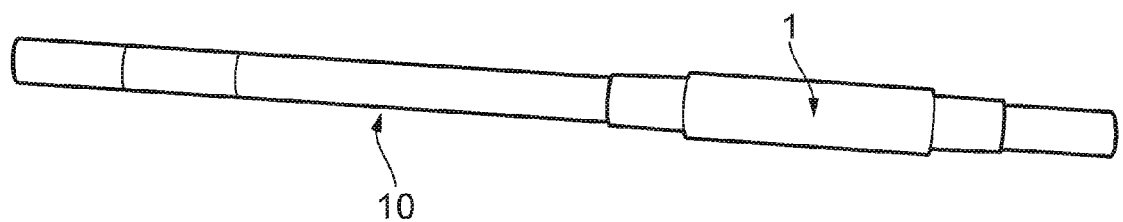
FIG. 2 is a picture of a sleeve in combination with a cryogenic straw.

FIG. 2 shows a sleeve 1 in combination with a cryogenic straw 10. The inner diameter of the sleeve is comparable to the outer diameter of the straw so that the sleeve forms a push fit around the straw. As can be seen in FIG. 2, the sleeve 1 surrounds the entire outer circumference of the straw 10. The sleeve 1 surrounds the outer circumference of the straw along the entire length of the tubular body 2 of the sleeve 1. When the sleeve 1 is provided around the straw 10, the ends of the straw 10 remain open.

Figure 3:
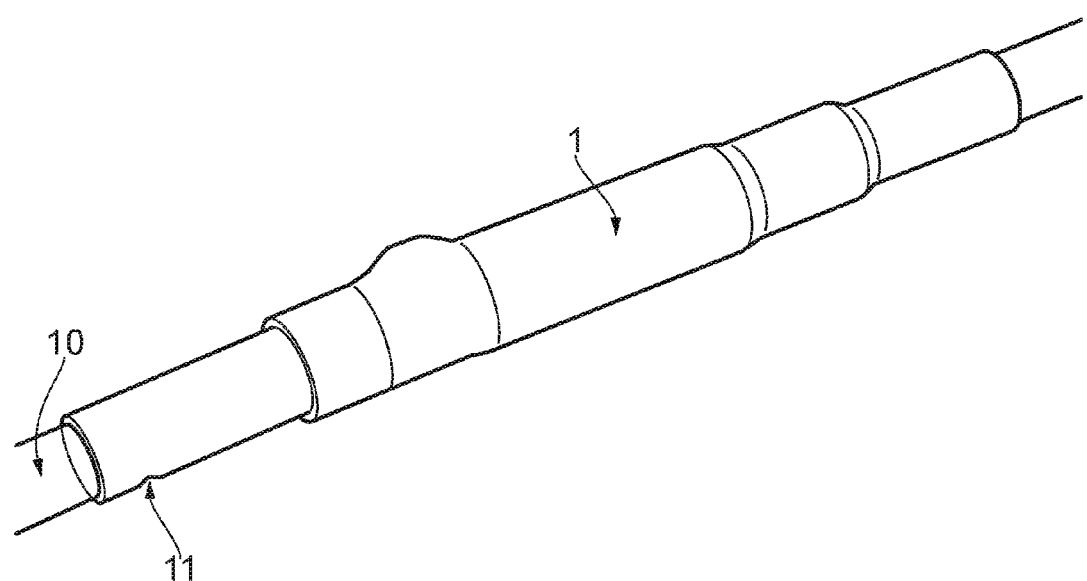
FIG. 3 is a picture of a sleeve crimped to a cryogenic straw.

FIG. 3 shows a sleeve 1 which has been crimped to the cryogenic straw 10. The crimp 11 forms a secure attachment between the sleeve and the straw to prevent the sleeve from sliding off the straw. In addition to acting as a securing means, the crimp acts as a locating means so that if the sleeve is removed from the straw with force it can be re-positioned in the same location.

In the embodiment shown in FIG. 3, the crimp 11 takes the form of a depression in the tubular body 2 of the sleeve 1 and a corresponding depression in the cryogenic straw 10. The depression in the tubular body 2 of the sleeve protrudes inwardly from the inner surface of the tube towards the cylindrical axis of the tube. This protrusion mates with the corresponding depression in the outer surface of the straw to form a securing and locating means.

Once the sleeve has been attached to the straw, the biological material can be inserted into the straw. The RFID chip can then be programmed i.e. a (world wide) unique reference identification can be written to the tag (and hence the straw).

Preferably, the number of loops in the coil of the antenna 4 lies within the range of 50-85 loops. Even more preferably, the number of loops of the antenna lies within the range of 65-70 loops.

The RFID tag can be positioned at any location along the length of the sleeve.

The material of the tubular body 2 is chosen to withstand cryogenic temperatures such as −196° C. Suitable materials include polyethylene or polypropylene. A handwritten or printed label may be wrapped around the tubular body so that the sleeve (and hence the straw) can be identified visually as well as electronically. The printed label may include a barcode.

The foregoing description of the preferred embodiments of the invention have been presented for purposes of illustration and description, it is not intended to be exhaustive or to limit the invention to the precise form disclosed, and modifications and variations are possible in light of the above teachings.

It is intended that the scope of the invention be defined by the claims appended hereto.

The invention claimed is:

1. A sleeve for a cryogenic straw, the sleeve comprising:
   a tubular body having a thickness of less than or equal to 0.5 mm and a length in a longitudinal direction, the tubular body including:
   a first end having a first orifice; and
   a second end that is opposite the first end and that has a second orifice, the tubular body being open through the length between the first orifice and the second orifice; and
   a radio-frequency identification (RFID) tag included in or attached to a surface of the tubular body.

2. The sleeve of claim 1 wherein the tubular body has a circular cross section along a plane perpendicular to its longitudinal axis.

3. The sleeve of claim 1, wherein the tubular body is rigid.

4. The sleeve of claim 1, wherein the tubular body has an inner diameter which is no less than 3.9 mm and no more than 4 mm.

5. The sleeve of claim 1, wherein the length along its longitudinal axis which is no less than 2 mm and no more than 135 mm.

6. The sleeve of claim 1, wherein the RFID tag is attached to the sleeve by an outer tubing.

7. The sleeve of claim 6, wherein the outer tubing includes heat shrink tubing.

8. An apparatus comprising:
 a cryogenic straw; and
 a sleeve for the cryogenic straw, the sleeve comprising:
  a tubular body having a thickness of less than or equal to 0.5 mm and a length in a longitudinal direction, the tubular body including:
   a first end having a first orifice, and
   a second end that is opposite the first end and that has a second orifice, the tubular body being open through the length between the first orifice and the second orifice; and
  a radio-frequency identification (RFID) tag included in or attached to a surface of the tubular body, wherein the sleeve surrounds a circumference of the cryogenic straw.

9. The apparatus of claim 8, wherein the sleeve is crimped to the cryogenic straw.

10. A method of labelling a cryogenic straw, the method comprising:
 sliding a sleeve onto the cryogenic straw, the sleeve having an integral RFID tag and a tubular body, the tubular body including:
  a first end having a first orifice; and
  a second end that is opposite the first end and that has a second orifice, the tubular body being open through a length of the tubular body between the first orifice and the second orifice; and
 crimping the sleeve onto the straw.

11. The method of claim 10, further comprising introducing a biological sample into the straw via suction after sliding the sleeve onto the straw.

12. An apparatus for labelling a cryogenic straw, the apparatus comprising:
 a sleeve for a cryogenic straw, the sleeve comprising:
  a tubular body having a thickness of less than or equal to 0.5 mm and a length in a longitudinal direction, the tubular body including:
   a first end having a first orifice; and
   a second end that is opposite the first end and that has a second orifice, the tubular body being open through the length between the first orifice and the second orifice;
  a radio-frequency identification (RFID) tag included in or attached to a surface of the tubular body; and
 an outer sleeve that includes:
  an outer-sleeve tubular body; and
  an outer-sleeve open end at each side of the outer-sleeve tubular body, wherein the RFID tag is secured between the sleeve and the outer sleeve.

13. A sleeve for a cryogenic straw, the sleeve comprising:
 an elongate hollow tubular body, the elongate hollow tubular body including:
  a first end having a first orifice; and
  a second end that is opposite the first end and that has a second orifice, the elongate hollow tubular body being open through its length between the first orifice and the second orifice; and
 an RFID tag mounted to an outer surface of the elongate hollow tubular body, wherein the sleeve is rigid and has a thickness of no more than 5 mm.

14. The sleeve of claim 13, wherein the tubular body has an inner diameter which is no less than 3.9 mm and no more than 4 mm.

15. The sleeve of claim 13, further comprising a protective coating which covers the RFID tag to attach the RFID tag to the tubular body.

* * * * *